United States Patent [19]

Sanderson et al.

[11] Patent Number: 4,900,850
[45] Date of Patent: Feb. 13, 1990

[54] RECOVERY OF PURIFIED DITERTIARY BUTYL PEROXIDE

[75] Inventors: John R. Sanderson, Leander; Robert A. Meyer, Austin, both of Tex.

[73] Assignee: Texaco Inc., White Plains, N.Y.

[21] Appl. No.: 945,628

[22] Filed: Dec. 23, 1986

[51] Int. Cl.$^4$ .......................................... C00F 301/19
[52] U.S. Cl. ..................................... 549/529; 568/577; 568/578; 568/909; 568/910.5; 568/9.3
[58] Field of Search ............... 568/576, 577, 578, 558, 568/910.5, 9.3; 549/529, 538; 203/44, 45

[56] References Cited

U.S. PATENT DOCUMENTS

| | | |
|---|---|---|
| 2,862,973 | 12/1958 | Winkler et al. ...................... 568/910 |
| 3,351,635 | 11/1967 | Kollar .................................. 568/850 |
| 3,449,219 | 6/1969 | Schmidt .............................. 549/529 |
| 3,474,151 | 10/1969 | Grave .................................. 549/529 |
| 4,810,809 | 3/1989 | Sanderson et al. ................. 549/529 |

Primary Examiner—Bruce Gray
Attorney, Agent, or Firm—Jack H. Park; Kenneth R. Priem; Carl G. Ries

[57] ABSTRACT

It has been discovered in accordance with the present invention that a tertiary butyl alcohol/ditertiary butyl peroxide azeotrope may be recovered from a product containing tertiary butyl alcohol and ditertiary butyl peroxide by distilling the tertiary butyl alcohol product to obtain an overhead fraction containing substantially all of the ditertiary butyl peroxide as a ditertiary butyl peroxide/tertiary butyl alcohol azeotrope and other contaminants.

It has been further discovered in accordance with the present invention that the ditertiary butyl peroxide can be recovered from the distillate fraction by extraction with water (e.g., in a countercurrent water extraction tower) to provide a ditertiary butyl peroxide product of any desired degree of purity.

11 Claims, 1 Drawing Sheet

RECOVERY OF PURIFIED DITERTIARY BUTYL PEROXIDE

BACKGROUND OF THE INVENTION

1. Field of the Invention

This invention relates to the recovery of purified ditertiary butyl peroxide from a feedstock containing a minor amount of ditertiary butyl peroxide. More particularly, this invention relates to a method for the recovery and purification of ditertiary butyl peroxide from a feedstock comprising a major amount of tertiary butyl alcohol and only a minor amount of ditertiary butyl peroxide. Still more particularly, this invention relates to a method wherein ditertiary butyl peroxide is recovered from a feedstock obtained by the oxidation of isobutane to provide a reaction mixture comprising unreacted isobutane, tertiary butyl alcohol, tertiary butyl hydroperoxide and a minor amount of ditertiary butyl peroxide or a reaction mixture obtained by the peroxidation of tertiary butyl hydroperoxide with propylene and comprising tertiary butyl alcohol, unreacted tertiary butyl hydroperoxide, ditertiary butyl peroxide, acetone and other contaminants.

2. Prior Art

It is known to react oxygen with isobutane to form a peroxidation reaction product wherein the principal peroxide that is formed is tertiary butyl hydroperoxide. However, a minor constituent of such a reaction product is ditertiary butyl peroxide, which is a valuable commercial product used, for example, as a high temperature free radical initiator in chemical reactions.

Conventionally, ditertiary butyl peroxide is prepared by the reaction of tertiary butyl alcohol or isobutylene with tertiary butyl hydroperoxide in the presence of an acid catalyst.

The coproduction of propylene oxide together with a coproduct, such as tertiary butyl alcohol, is summarized in an article "Propylene Oxide by the Coproduct Process" by Landau et al. (Chem. Tech., Oct. 1979, pp. 602–607).

The process is described in greater detail in Kollar U.S. Pat. Nos. 3,350,422 and 3,351,635 which are directed to the catalytic epoxidation of an olefin by reaction with a hydroperoxide such as tertiary butyl hydroperoxide. When the olefin is propylene and the hydroperoxide is tertiary butyl hydroperoxide, the principal reaction products are propylene oxide and tertiary butyl alcohol.

Herzog U.S. Pat. No. 3,928,393 is directed to an improvement in the Kollar et al. process wherein citric acid is used to minimize iron catalyzed decomposition of the organic hydroperoxide. This patent includes examples directed to the preparation of tertiary butyl hydroperoxide by the reaction of isobutane with oxygen.

Grane U.S. Pat. No. 3,474,151 is also directed to the oxidation of isobutane with oxygen to provide tertiary butyl alcohol and discloses that the reaction mixture contains not only tertiary butyl hydroperoxide, but also ditertiary butyl peroxide. In their U.S. Pat. No. 4,239,926, Grane et al. disclose a method for significantly drying the tertiary butyl alcohol prepared by the oxidation of isobutane, the method involving extractive distillation of the tertiary butyl alcohol product using a specially proportioned blend of xylene, acetone and water as the extractant.

Harvey U.S. Pat. No. 3,449,217 is directed to a method for the recovery of tertiary butyl hydroperoxide from a mixture of tertiary butyl hydroperoxide and tertiary butyl alcohol. However, nothing is said in the patent about the recovery and purification of the ditertiary butyl peroxide.

SUMMARY OF THE INVENTION

Ditertiary butyl peroxide is a stable article of commerce which is used, for example, as a high temperature free radical initiator.

When isobutane is reacted with molecular oxygen, the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl peroxide but tends to distill overhead, which suggests that it forms a minimum boiling azeotrope with another component or components.

Tertiary butyl hydroperoxide is useful as a raw material for the manufacture of tertiary butyl alcohol either by decomposition of the tertiary butyl hydroperoxide as such, or by the catalytic reaction of tertiary butyl hydroperoxide with an olefin such as propylene to form an epoxide and tertiary butyl alcohol. When the olefin is propylene, the coproduct is propylene oxide. The reaction conditions used for the conversion of tertiary butyl hydroperoxide, by either process, to tertiary butyl alcohol are such that the ditertiary butyl peroxide normally is not consumed or destroyed and remains in the reaction mixture as an impurity. Only a minor amount of the peroxidation reaction mixture formed by the reaction of molecular oxygen with isobutane will be composed of ditertiary butyl peroxide. However, this minor amount may constitute as much as about 0.5 wt. % of the total peroxidation reaction mixture.

For example, when tertiary butyl hydroperoxide is recovered from the peroxidation reaction mixture obtained by the reaction of molecular oxygen with isobutane, the ditertiary butyl peroxide will also normally be present as a contaminant. Therefore, when the tertiary butyl hydroperoxide is reacted with propylene to form propylene oxide and tertiary butyl alcohol, the ditertiary butyl peroxide will be present in the reaction mixture and in the reaction product.

The product of the reaction of tertiary butyl hydroperoxide with propylene is normally separated into useful components, usually by distillation, to form, for example, sequential distillate fractions composed of unreacted propylene, propylene oxide and tertiary butyl alcohol. The ditertiary butyl hydroperoxide will normally be present in the recovered tertiary butyl alcohol as a contaminant together with other contaminants such as residual tertiary butyl hydroperoxide, acetone, methyl formate, methanol, tertiary butyl formate, isopropyl alcohol, etc.

It has been discovered in accordance with the present invention that tertiary butyl alcohol and ditertiary butyl peroxide form an azeotrope containing about equal parts by weight of each component which has a boiling point at 50 mm of mercury of about 24.7° C. It has further been discovered in accordance with the present invention that the tertiary butyl alcohol/ditertiary butyl peroxide azeotrope may be recovered from a product containing tertiary butyl alcohol, ditertiary butyl peroxide and other contaminants by distilling the tertiary butyl alcohol product to obtain an overhead fraction containing substantially all of the ditertiary butyl peroxide/tertiary butyl alcohol azeotrope and other contaminants. The distillation cut point for the overhead fraction can vary, but should be a cut point such that the distillate fraction will contain at least about 50 wt. % of tertiary butyl alcohol. When the cut point is selected such that the distillate fraction contains more tertiary butyl alcohol (e.g., from about 50 to about 65% tertiary butyl alcohol), substantially all of the ditertiary butyl peroxide that is initially present in the tertiary butyl alcohol feed to the distillation unit will be present in the distillate fraction.

It has been further discovered in accordance with the present invention that the ditertiary butyl peroxide can be recovered from the distillate fraction by extraction with water (e.g., in a countercurrent water extraction tower) to provide a ditertiary butyl peroxide product of any desired degree of purity. Normally, the ditertiary butyl peroxide product that is obtained by the water extraction step will contain at least a minor amount of tertiary butyl alcohol.

When such is the case, in accordance with the present invention, the ditertiary butyl peroxide extract containing the residual quantities of tertiary butyl alcohol is fractionally distilled to provide a light fraction comprising a tertiary butyl alcohol/ditertiary butyl peroxide azeotrope and a heavier fraction consisting essentially of ditertiary butyl peroxide.

Figure 1:
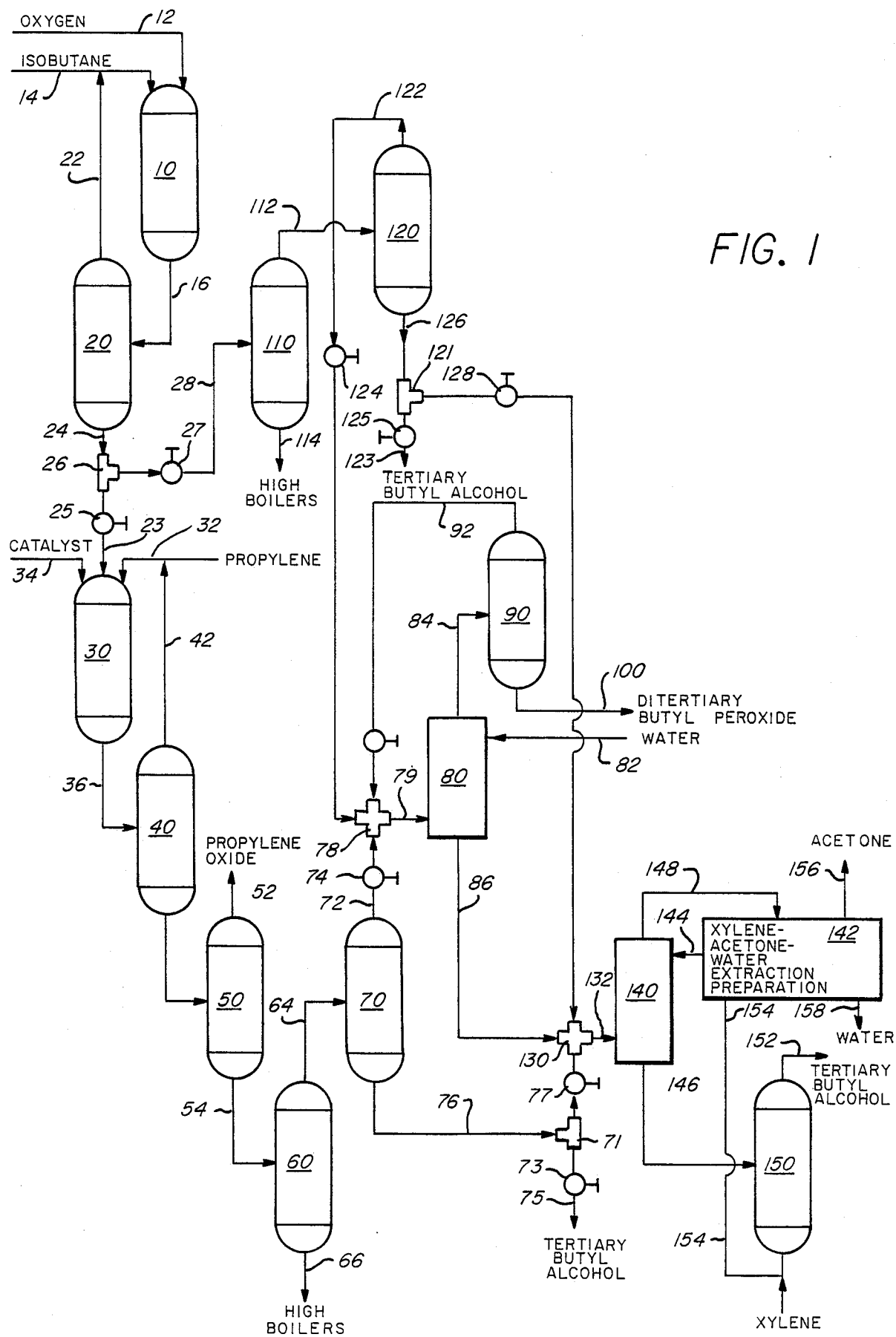
FIG. 1 is a schematic flow sheet with conventional parts omitted showing the general reaction and recovery sequence that is used in the practice of a preferred embodiment of the present invention.

In the drawing, for convenience, the present invention is illustrated in connection both with a process wherein the desired reaction product is tertiary butyl alcohol and also a process wherein propylene oxide is produced as a coproduct together with tertiary butyl alcohol. It will be understood that in normal commercial practice only one of the processes will be used, or if both processes are practiced, that they will be practiced in separate units.

DESCRIPTION OF THE PREFERRED EMBODIMENT

Turning now to FIG. 1, there is shown a schematic flow sheet illustrating a preferred method of practicing the process of the present invention. In the drawing, conventional parts such as valves, pumps, temperature sensors, pressure sensors, heaters, coolers, control and flow regulation apparatus, reboilers, reflux condensers, etc., have been omitted.

In accordance with the present invention, an appropriate reactor 10 is charged with oxygen by way of a charge line 12 and with isobutane and a catalyst (e.g., a known molybdenum catalyst) by way of a charge line 14 from appropriate sources (not shown) such as storage tanks. Within the reactor 10, and in accordance with known prior art procedures, the oxygen catalytically reacts with a portion of the isobutane to provide a reaction mixture which is discharged from the reactor 10 by way of a discharge line 16. The reaction mixture 16 comprises, for example, unreacted isobutane, tertiary butyl alcohol and minor quantities of other reaction components and byproducts including ditertiary butyl peroxide and may also comprise a significant quantity of tertiary butyl hydroperoxide.

If the only primary product to be manufactured is tertiary butyl alcohol, the reaction conditions used in the reactor 10 will be selected so that the tertiary butyl hydroperoxide is converted directly to tertiary butyl alcohol, as disclosed for example, in Worrell U.S. Pat. No. 4,296,263 or, in the alternative, the decomposition of the tertiary butyl hydroperoxide is accomplished in a separate digestion zone (not shown), as described for example in Grane et al. U.S. Pat. No. 4,294,999 or Grane et al. U.S. Pat. No. 4,296,262.

The reaction mixture 16 is charged to a first distillation zone 20, such as a simple flash zone, wherein the reaction mixture is separated into a lighter fraction 22 comprising unreacted isobutane for recycle to isobutane charge line 14. A heavier fraction 24 discharged from first distillation zone 20 comprises t-butanol and by-products, including ditertiary butyl peroxide, acetone, methanol, methyl formate, tertiary butyl formate, isopropyl alcohol, etc.

If desired, the distillate fraction 22 may have a cut point such that a minor amount of tertiary butyl alcohol is taken overhead with the isobutane. If this is done, a portion of the byproduct water will also be taken overhead, thus partially drying the heavier fraction 24. In this instance, the t-butanol and water would be charged to a decanter (not shown) from which the isobutane rich stream would be recycled to the reaction zone 20. This is usually done if the fraction 24 is to be used as a feedstock for reaction of the tertiary butyl hydroperoxide with propylene to form propylene oxide and additional tertiary butyl alcohol because it is normally desirable, in this situation, to use a feedstock containing about 0.5 wt. % or less of water.

The heavier fraction 24 is charged to a three-way junction 26. If the fraction 24 is a reaction product to be used primarily for the production of tertiary butyl alcohol (and contains only a minor amount of tertiary butyl hydroperoxide), it is discharged from three-way junction 26 by a branch line 28 controlled by a valve 27 to be processed in a manner to be described.

In accordance with one preferred embodiment of the present invention, the heavier fraction 24 contains a significant amount of tert. butyl hydroperoxide and is discharged from three-way junction 26 by a line 23 controlled by a valve 25 leading to a second reactor 30.

Propylene from a suitable source (not shown) is also charged to reactor 30 by a charge line 32 and an appropriate catalyst (e.g., a propylene glycol solution of a soluble molybdenum catalyst such as molybdenum glycolate), is charged by way of a catalyst charge line 34.

Within the reactor 30, propylene is catalytically reacted with tertiary butyl hydroperoxide, in accordance with known procedures, to provide a reaction mixture which is discharged by way of a discharge line 36 and is composed of unreacted propylene, tertiary butyl alcohol, propylene oxide, and byproducts, including not only the ditertiary butyl peroxide initially charged by way of line 23, but also impurities, principally acetone, methanol, methyl formate, propylene glycol, glycol ethers, etc., formed during the course of the epoxidation reaction. The reaction mixture 36 is charged to a second distillation zone 40, for example, wherein unreacted propylene is recovered overhead by way of a line 42 for recycle to the propylene charge line 32 for the reactor 30 and a bottoms fraction 44 which is charged to a third distillation zone 50.

An overhead propylene oxide fraction 52 is recovered from the distillation zone 50 and the bottom products are discharged by a line 54 leading to a fourth distillation zone 60 where the fraction 54 is separated into a bottoms fraction 62 comprising catalyst and other heavy residue which may be purged from the system. In addition, an overhead fraction 64 is obtained which is composed primarily of tertiary butyl alcohol but which also contains the intermediate impurities including ditertiary butyl peroxide and hydroperoxide impurities, acetone, and other oxygenated impurities formed in reactor 30.

In accordance with this embodiment of the present invention, the fraction 64 is charged to a fifth distillation zone 70.

In fifth distillation zone 70 a distillate fraction is obtained containing a tertiary butyl alcohol/ditertiary butyl peroxide azeotrope and comprising about 50 to about 65 wt. % of tertiary butyl alcohol, and substantially all of the ditertiary butyl peroxide, together with other impurities that boil overhead therewith. The distillate fraction is discharged from the fifth distillation zone 70 by a line 72 controlled by a valve 74.

A bottoms fraction 76 composed of tertiary butyl alcohol and residual impurities is discharged by way of line 76 leading to a three-way junction 71 for discharge or further treatment in a manner to be described.

In accordance with the present invention, the fraction 72 is charged to a first four-way junction 78 and then by a feed line 79 to the bottom of a water extraction zone, such as a packed water extraction column 80. Water is charged to the column 80 by way of a water charge line 82 for countercurrent contact with the azeotrope feed-fraction 79 fed to the bottom of the tower. As a consequence of the countercurrent contact, a raffinate phase 84 is formed which is taken overhead and an extract phase 86 is formed, which is composed of water, tertiary butyl alcohol and other impurities. The extract is suitably discharged by line 86 for further processing.

By way of example, about 100 pounds per hour of a mixture of about 50 wt. % of tertiary butyl alcohol with about 50 wt. % of ditertiary butyl peroxide may be charged to the water extraction tower 80 by line 79 and about 50 pounds per hour of water may be charged to the water extraction tower 80 by line 82. The water-lean ditertiary butyl peroxide raffinate 84 from the water extraction tower 80, in this instance may comprise, for example, about 98.5 wt. % of ditertiary butyl peroxide, about 1 wt. % of tertiary butyl alcohol and about 0.5 wt. % of water. The water-rich extract solution 86 discharged from water extraction zone 80 by line 86, in this instance, may comprise about 99.5 wt. % of a mixture of about equal parts by weight of tertiary butyl alcohol and water and about 0.5 wt. % of ditertiary butyl peroxide.

The raffinate phase 84 from water extraction zone 80 is suitably fed to a sixth distillation zone 90 where it is separated into an overhead distillate fraction comprising a tertiary butyl alcohol/ditertiary butyl peroxide azeotrope 92 which, if desired, may be recycled to first four-way junction 78.

The higher boiling fraction 100 discharged from the sixth distillation zone 90 will be composed primarily of ditertiary butyl hydroperoxide, the degree of purity being, for example, from 85 to 99%, depending upon the efficiency with which the water extraction tower 80 is operated.

The second, third, fourth and fifth distillation zones 40, 50, 60 and 70 may be operated as a multi-stage distillation zone and, in practice, may contain either a greater or a lesser number of distillation towers, depending on the particular distillation engineering design that is used.

In accordance with another embodiment of the present invention, the valves 25, 74 and 77 are closed and the valve 27 is opened so that the fraction 24 after being charged to first three-way junction 26 is then charged by line 28 to a seventh distillation zone 110 wherein a lighter tertiary butyl alcohol fraction 112 is obtained. The fraction 112 is comprised principally of tertiary butyl alcohol, but will also contain intermediate impurities including ditertiary butyl peroxide, tertiary butyl hydroperoxide, acetone and other oxygenated impurities formed in the reactor 10. A bottoms fraction comprising catalyst and higher boiling residue components is discharged from seventh distillation zone 110 by line 114 and may be purged from the system.

In accordance with this embodiment of the present invention, the fraction 112 is charged to an eighth distillation zone 120. In eighth distillation zone 120, a distillate fraction 122 is obtained which is composed of a tertiary butyl alcohol/ditertiary butyl peroxide azeotrope comprising about 50 to 65 wt. % of tertiary butyl alcohol and substantially all of the ditertiary butyl peroxide formed in the reactor 10, together with other impurities that boil overhead therewith. The distillate fraction is discharged through line 122 controlled by valve 124 leading to first four-way junction 78.

A tertiary butyl alcohol fraction is discharged from eighth distillation zone 120 by a line 126 leading to three-way junction 121 for discharge or further processing in a manner to be described.

The tertiary butyl alcohol lines 76, 86 and 126 lead to a second four-way junction 130. When valve 25 in line 23 is open, valve 27 in line 28 will be closed, and in like manner, valve 77 will be open and valve 128 will be closed. Contrawise, when valves 25 and 77 are closed, valves 27 and 128 will be open.

If the tertiary butyl alcohol in line 76 has a sufficiently low water content (e.g., about 1.5 wt. % or less), the valve 77 may be closed and the valve 75 and discharge line 73 may be opened so that the tertiary butyl alcohol in line 76 may be recovered as product. Likewise, if the water content of the tertiary butyl alcohol in line 126 has an acceptably low water content, the valve 128 in line 126 may be closed and the valve 125 and discharge line 123 may be opened in order to recover the tertiary butyl alcohol in line 126 as product. Thus, the tertiary butyl alcohol fed to the four-way junction 130 will comprise fraction 86 and may also comprise either fraction 76 or fraction 126.

reaction mixture composed principally of tertiary butyl alcohol from which unreacted propylene and propylene oxide had been removed. The resulting product was used as a starting material for the present example.

EXAMPLE 1

In order to demonstrate the need for obtaining the tertiary butyl alcohol/ditertiary butyl peroxide azeotrope fraction described above, the tertiary butyl alcohol starting material obtained from the reaction of propylene oxide with tertiary butyl hydroperoxide, as described above, was sequentially extracted in a batch water extractor. In each extraction, 15 grams of raffinate or upper layer was extracted with the amount of water as indicated in Table I.

TABLE I

| | Extraction of TBA Distillate[a] | | | | | | |
|---|---|---|---|---|---|---|---|
| | Start. | 1st Extraction[b] | | 2nd Extraction[c] | | 3rd Extraction[b] | |
| Starting Material | Material | Upper Layer | Lower Layer | Upper Layer | Lower Layer | Upper Layer | Lower Layer |
| Isobutane | 0.344 | 0.044 | 0.211 | 0.046 | 0.025 | 0.231 | 0 |
| Methyl Formate | 8.192 | 4.781 | 7.416 | 3.581 | 5.470 | 5.204 | 6.121 |
| Isobutylene Oxide | 0.380 | 0.294 | 0.009 | 0.284 | 0.014 | 0.370 | 0.208 |
| Acetone | 14.359 | 10.340 | 17.299 | 7.156 | 18.731 | 5.640 | 16.567 |
| Isobutyraldehyde | 0.196 | 0.155 | 0.180 | 0.163 | 0.162 | 0.228 | 0.110 |
| Methyl t-Butyl Peroxide | 0.698 | 0.661 | 0.414 | 0.880 | 0.272 | 1.486 | 0.080 |
| Methanol | 1.039 | 0.674 | 1.124 | 0.366 | 1.210 | 0.249 | 0.893 |
| t-Butyl Alcohol | 58.128 | 62.817 | 63.519 | 60.494 | 67.445 | 46.631 | 72.446 |
| t-Butyl Formate/ IPA | 5.828 | 6.663 | 4.120 | 8.346 | 3.431 | 11.000 | 2.051 |
| t-Butyl i-Pr Peroxide | 0.393 | 0.487 | 0.169 | 0.674 | 0.068 | 1.091 | 0.015 |
| Di-tert-Butyl Peroxide | 7.782 | 10.220 | 3.242 | 14.714 | 1.292 | 23.095 | 0.183 |

[a]6071-27-20
[b]15 g Distillate extracted with 10 g H$_2$O
[c]Extracted with 2 g H$_2$O
[d]Extracted with 2.3 g H$_2$O
N.B. No. 6064-85

A feed line 132 leads from four-way junction 130 to an extractive distillation zone 140 which, in the illustrated embodiment, may be constructed and operated in the manner disclosed in Grane et al. U.S. Pat. No. 4,239,926. In order to remove most of the water present in the tertiary butyl alcohol, the tertiary butyl alcohol feed 132 is counter-currently contacted in extractive distillation zone 140 with an extractant composed primarily of xylene, but also containing controlled amounts of acetone and water. The extractant is prepared in a xylene/acetone/water extractant preparation zone 142 in the manner taught by Grane et al. and then charged to the extractive distillation zone 140 by an extractant charge line 144. A bottoms fraction 146 is withdrawn from extractive distillation zone 140 and charged to a ninth distillation zone 150 where it is separated into a tertiary butyl alcohol product fraction 152 containing less than about 1.5 wt. % of water and a bottoms recycle fraction 154 which is returned to the extractant preparation zone 142. The overhead fraction 148 from extractive distillation zone 140 is also returned to extractant preparation zone 142. Excess acetone is discharged from the extractant preparation zone 142 by a discharge line 156 and excess water is discharged by a line 158.

EXAMPLES

In order to demonstrate the improvement obtainable with the process of the present invention, a feedstock was used obtained by the catalytic reaction of propylene with tertiary butyl hydroperoxide to provide a Turning now to Table I, it will be noted that the starting material that was used was composed principally of tertiary butyl alcohol, but contained a significant quantity of acetone and significant quantities of both methyl formate and ditertiary butyl peroxide. Contaminating quantities of isobutane, isobutylene oxide, isobutyraldehyde, methyl t-butyl peroxide, methanol, a t-butyl formate/isopropyl alcohol doublet and t-butyl isopropyl peroxide were also present in the feed material. It will be noted that in the three extractions that were sequentially performed, the extract progressively contained a higher percentage of ditertiary butyl hydroperoxide so that, for example, the third stage extract contained 23% ditertiary butyl peroxide, a three-fold concentration increase as compared with the starting material. However, the extract still contained a very significant quantity (46.6%) of tertiary butyl alcohol as well as other materials.

EXAMPLE 2

Since the principal contaminant in the feed material of the present invention is acetone, in order to more easily illustrate the advantage of the present invention, a synthetic feedstock fraction was prepared, having the composition set forth in Table II, namely, about 5 wt. % of acetone, about 29 wt. % of tertiary butyl alcohol and about 65 wt. % of ditertiary butyl peroxide. The starting material was subjected sequentially to four batch water extractions under ambient conditions using equal parts by weight of the starting material and water for each extraction. Note that by the end of the fourth extraction, the upper layer (raffinate) contained 88.4 wt. % of ditertiary butyl peroxide, only about 10% by weight of tertiary butyl alcohol and less than 1 wt. % of acetone.

TABLE II

| Extraction of Acetone/TBA/DTBP with Water[a] | | | |
|---|---|---|---|
| N.B. 6064-94 | Acetone[b] | TBA[b] | DTBP[b] |
| Starting Material | 5.044 | 29.595 | 65.054 |
| First Extraction | | | |
| Upper Layer | 3.975 | 25.991 | 69.717 |
| Lower Layer | 25.441 | 73.559 | 0.636 |
| Second Extraction | | | |
| Upper Layer | 2.324 | 20.114 | 77.302 |
| Lower Layer | 21.742 | 77.572 | 0.334 |
| Third Extraction | | | |
| Upper Layer | 1.325 | 14.492 | 83.878 |
| Lower Layer | 17.421 | 81.840 | 0.207 |
| Fourth Extraction | | | |
| Upper Layer | 0.955 | 10.267 | 88.413 |
| Lower Layer | 13.181 | 85.869 | 0.257 |

[a]25.0 g DTBP, 10.0 g TBA, and 3.0 g Acetone extracted 4 times with water (10.0 g)
[b]Percent determined by GC The results of Table II demonstrate that water extraction of the tertiary butyl alcohol/ditertiary butyl peroxide azeotrope described above provides a feasible method for obtaining purified ditertiary butyl peroxide.

It will be understood that the degree of purity that is desired can be obtained by the number of stages of water extraction that are utilized.

EXAMPLE 3

In order to demonstrate that ditertiary butyl peroxide can be recovered from the TBA/ditertiary butyl peroxide azeotrope, a synthetic azeotrope was prepared having the composition as a starting material as set forth in Table IV, namely about 53.3 wt. % tertiary butyl alcohol and about 46.4 wt. % ditertiary butyl peroxide.

The feed material was subjected to six sequential batch extractions utilizing about equal parts by weight of water and feed material for each extraction. Note that by the end of the sixth extraction, the upper layer contained substantially all of the ditertiary butyl peroxide and less than 1 wt. % of tertiary butyl alcohol whereas the lower layer contained substantially all of the tertiary butyl alcohol and less than 1 wt. % of ditertiary butyl peroxide.

TABLE III

| Extraction of DTBP/TBA with Water[a] | | |
|---|---|---|
| N.B. 6089-9 | TBA[b] | DTBP[b] |
| Starting Material | 53.291 | 46.423 |
| First Extraction | | |
| Upper Layer | 47.157 | 52.567 |
| Lower Layer | 99.257 | 0.537 |
| Second Extraction | | |
| Upper Layer | 37.708 | 62.039 |
| Lower Layer | 99.324 | 0.353 |
| Third Extraction | | |
| Upper Layer | 26.370 | 73.310 |
| Lower Layer | 99.522 | 0.250 |
| Fourth Extraction | | |
| Upper Layer | 13.706 | 85.934 |
| Lower Layer | 99.730 | 0.270 |
| Fifth Extraction | | |
| Upper Layer | 3.830 | 95.839 |
| Lower Layer | 99.725 | 0.275 |
| Sixth Extraction | | |
| Upper Layer | 0.808 | 98.803 |
| Lower Layer | 99.233 | 0.767 |

[a]25 ml TBA and 25 ml DTBP extracted 6 × 20 ml water.
[b]Determined by GC. Water not seen on this column.

The foregoing experiments are presented by way of example only, and are not intended as limitations of the scope of this invention.

Having thus described our invention, what is claimed is:

1. A method for the recovery of ditertiary butyl peroxide from a mixture of a minor amount of ditertiary butyl peroxide with a larger amount of tertiary butyl alcohol which comprises the steps of:
    charging said mixture to a distillation zone and separating a lighter distillate ditertiary butyl peroxide/tertiary butyl alcohol azeotrope fraction from said mixture therein, and
    resolving said ditertiary butyl peroxide/tertiary butyl alcohol azeotrope by water extraction into a raffinate fraction consisting essentially of ditertiary butyl peroxide and an extract fraction comprising water, ditertiary butyl peroxide and tertiary butyl alcohol.

2. In a method wherein isobutane is reacted with oxygen to provide a reaction product comprising unreacted isobutane, tertiary butyl hydroperoxide and tertiary butyl alcohol as principle reaction products, and ditertiary butyl peroxide as a minor reaction product the improvement for recovering substantially pure ditertiary butyl peroxide from said reaction product which comprises the steps of:
    charging said reaction product to a distillation zone and separating an unreacted isobutane distillate fraction and a ditertiary butyl peroxide/tertiary butyl alcohol azeotrope distillate fraction therefrom, and
    charging said ditertiary butyl peroxide/tertiary butyl alcohol azeotrope fraction to a water extraction zone and resolving said ditertiary butyl peroxide/tertiary butyl alcohol azeotrope therein by water extraction therein into a raffinate fraction consisting essentially of ditertiary butyl peroxide and an extract fraction comprising water, ditertiary butyl peroxide and tertiary butyl alcohol.

3. A method as in claim 2 wherein the ditertiary butyl peroxide/tertiary butyl alcohol azeotrope fraction contains from about 50 to about 65 wt. % of tertiary butyl alcohol.

4. In a process wherein a feed material comprising principal amounts of tertiary butyl hydroperoxide and tertiary butyl alcohol and a minor amount of ditertiary butyl peroxide is charged to a reactor together with propylene and a soluble epoxidation catalyst and wherein at least a portion of the propylene is reacted in said reactor with said tertiary butyl hydroperoxide to form a reaction product composed of unreacted feed components, propylene oxide and an additional quantity of tertiary butyl alcohol, the improvement for recovering substantially pure ditertiary butyl peroxide from said reaction product which comprises the steps of:
    charging said reaction product to a distillation zone and recovering therein a distillate unreacted propylene fraction, a distillate propylene oxide product fraction, a distillate ditertiary butyl peroxide/tertiary butyl alcohol azeotrope fraction and a tertiary butyl alcohol fraction, and charging said distillate ditertiary butyl peroxide/tertiary butyl alcohol azeotrope fraction to a water extraction zone and resolving said ditertiary butyl peroxide/tertiary butyl alcohol azeotrope fraction therein by water extraction into a raffinate fraction consisting essentially of ditertiary butyl peroxide and an extract fraction comprising water, ditertiary butyl peroxide and tertiary butyl alcohol.

5. A method as in claim 4 wherein the ditertiary butyl peroxide/tertiary butyl alcohol azeotrope fraction contains from about 50 to about 65 wt. % of tertiary butyl alcohol.

6. A method as in claim 4 wherein said raffinate fraction is charged to a second distillation zone and fractionated therein to provide a lighter ditertiary butyl peroxide/tertiary butyl alcohol azeotrope distillate fraction and a heavier fraction consisting essentially of ditertiary butyl peroxide and wherein said lighter azeotrope fraction is recycled to said water extraction zone.

7. In a process wherein a feed material comprising principal amounts of tertiary butyl hydroperoxide and tertiary butyl alcohol and a minor amount of ditertiary butyl peroxide is charged to a reactor together with propylene and a soluble epoxidation catalyst and wherein at least a portion of the propylene is reacted in said reactor with said tertiary butyl hydroperoxide to form a reaction product composed of unreacted feed components, propylene oxide and an additional quantity of tertiary butyl alcohol, the improvement for recovering substantially pure ditertiary butyl peroxide from said reaction product after said reaction product is discharged from said reactor which comprises the steps of:

charging said reaction product to a first distillation zone and separating therein a first unreacted propylene distillate fraction, charging the remainder of said reaction product from said first distillation zone to a second distillation zone and separating a second propylene oxide distillate product fraction therein, charging the remaining heavier components of said reaction mixture from said second distillation zone to a third distillation zone and separating a third distillate fraction comprising a major amount of tertiary butyl alcohol and a minor amount of ditertiary butyl peroxide, charging said third distillate fraction from said third distillation zone to a fourth distillation zone and separating a fourth distillate ditertiary butyl peroxide tertiary butyl alcohol azeotrope fraction and a heavier tertiary butyl alcohol product fraction therein, charging said fourth distillate ditertiary butyl peroxide/tertiary butyl alcohol azeotrope fraction from said fourth distillation zone to a water extraction zone and resolving said ditertiary butyl peroxide/tertiary butyl alcohol azeotrope therein by water extraction into a raffinate fraction consisting essentially of ditertiary butyl peroxide and an extract fraction comprising water, ditertiary butyl peroxide and tertiary butyl alcohol, and recovering said second propylene oxide distillate fraction, said heavier tertiary butyl alcohol product fraction and said ditertiary butyl peroxide extract fraction.

8. A method as in claim 7 wherein said fourth ditertiary butyl peroxide/tertiary butyl alcohol azeotrope fraction contains from about 50 to about 65 wt. % of tertiary butyl alcohol.

9. A method as in claim 7 wherein said first propylene distillate fraction is recycled to said reaction zone.

10. A method for the continuous production of propylene oxide, tertiary butyl alcohol and ditertiary butyl peroxide which comprises the steps of:

a. continuously charging isobutane and oxygen to a first reaction zone and reacting oxygen with a portion of the isobutane therein to provide a first reaction product comprising unreacted isobutane, tertiary butyl hydroperoxide and tertiary butyl alcohol as principle reaction products, and ditertiary butyl peroxide as a minor reaction product, said ditertiary butyl peroxide being present in the ratio of about 1 part of ditertiary butyl peroxide per 10 to 20 parts of tertiary butyl hydroperoxide, b. continuously charging said first reaction product to a first distillation zone and separating an unreacted isobutane distillate recycle fraction therefrom, c. continuously recyling said unreacted isobutane distillate fraction to said first reaction zone, d. continuously charging the remainder of said first reaction product, comprising principle amounts of tertiary butyl hydroperoxide and tertiary butyl alcohol and a minor amount of ditertiary butyl peroxide, from said first distillation zone to a second reaction zone together with propylene and a soluble epoxidation catalyst and continuously reacting a portion of said propylene with said tertiary butyl hydroperoxide therein to form a second reaction product composed of unreacted components of said first reaction product, propylene oxide and an additional quantity of tertiary butyl alcohol, e. continuously charging said second reaction product to a multi-stage distillation zone and separating said second reaction product therein into a first unreacted propylene distillate fraction, a second propylene oxide distillate product fraction and a third distillate fraction comprising a major amount of tertiary butyl alcohol and a minor amount of ditertiary butyl hydroperoxide, f. continuously charging said third distillate fraction from said multi-stage distillation zone to a second distillation zone and separating therein a fourth distillate ditertiary butyl peroxide/tertiary butyl alcohol azeotrope fraction and a heavier tertiary butyl alcohol product fraction, said fourth distillate fraction containing from about 50 to about 65 wt. % of tertiary butyl alcohol, and g. continuously charging said fourth ditertiary butyl peroxide/tertiary butyl alcohol azeotrope fraction to a water extraction zone and resolving said ditertiary butyl peroxide/tertiary butyl alcohol azeotrope by water extraction therein into a raffinate fraction consisting essentially of ditertiary butyl peroxide and an extract fraction comprising water, ditertiary butyl peroxide and tertiary butyl alcohol, h. continuously recycling said first unreacted propylene distillate fraction to said second reaction zone, and i. continuously recovering said second propylene oxide distillate product fraction, said heavier tertiary butyl alcohol product fraction and said raffinate fraction.

11. A method as in claim 10 wherein said raffinate fraction is charged to a third distillation zone and fractionated therein to provide a lighter ditertiary butyl peroxide/tertiary butyl alcohol azeotrope distillate fraction and a heavier fraction consisting essentially of ditertiary butyl peroxide and wherein said lighter azeotrope fraction is recycled to said water extraction zone.

* * * * *